US011674953B2

(12) United States Patent
Renquist (10) Patent No.: US 11,674,953 B2
(45) Date of Patent: Jun. 13, 2023

(54) METHODS FOR MEASURING REDUCING EQUIVALENT PRODUCTION BY TISSUES TO DETERMINE METABOLIC RATES AND METHODS OF USE

(71) Applicant: ARIZONA BOARD OF REGENTS ON BEHALF OF THE UNIVERSITY OF ARIZONA, Tucson, AZ (US)

(72) Inventor: Benjamin J. Renquist, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 345 days.

(21) Appl. No.: 16/875,775

(22) Filed: May 15, 2020

(65) Prior Publication Data

US 2020/0278344 A1 Sep. 3, 2020

Related U.S. Application Data

(63) Continuation-in-part of application No. PCT/US2018/061349, filed on Nov. 15, 2018, which is a continuation of application No. 15/754,126, filed on Feb. 21, 2018, now abandoned, and a continuation-in-part of application No. 15/754,126, filed as application No. PCT/US2016/048006 on Aug. 22, 2016, now abandoned.

(60) Provisional application No. 62/586,578, filed on Nov. 15, 2017, provisional application No. 62/208,433, filed on Aug. 21, 2015.

(51) Int. Cl.
*G01N 33/52* (2006.01)
*G01N 33/50* (2006.01)
*G01N 33/18* (2006.01)
*A01K 67/02* (2006.01)
*C12Q 1/00* (2006.01)

(52) U.S. Cl.
CPC .......... *G01N 33/52* (2013.01); *A01K 67/02* (2013.01); *C12Q 1/008* (2013.01); *G01N 33/1806* (2013.01); *G01N 33/5005* (2013.01); *G01N 33/5088* (2013.01); *G01N 33/5097* (2013.01); *G01N 2333/43504* (2013.01); *G01N 2333/4603* (2013.01)

(58) Field of Classification Search
None
See application file for complete search history.

(56) References Cited

U.S. PATENT DOCUMENTS

| 2007/0015164 A1 | 1/2007 | Khatib |
| 2008/0040044 A1 | 2/2008 | Dunlay et al. |
| 2010/0197789 A1 | 8/2010 | Airma et al. |
| 2011/0321182 A1 | 12/2011 | Lehnert et al. |
| 2012/0221250 A1 | 8/2012 | Cottle |
| 2013/0251671 A1 | 9/2013 | Kaufman et al. |
| 2015/0344974 A1 | 12/2015 | Riggs et al. |

FOREIGN PATENT DOCUMENTS

| EP | 3337904 A1 | 7/2021 |
| KR | 20140140904 A | 12/2014 |
| WO | WO01/60152 A3 | 8/2001 |
| WO | WO0160152 A2 | 8/2001 |
| WO | WO2012167243 A1 | 12/2012 |
| WO | WO2017035064 A1 | 3/2017 |
| WO | WO2017187433 A1 | 11/2017 |
| WO | WO2018218161 A2 | 11/2018 |

OTHER PUBLICATIONS

Holst, C. Martina, and Stina M. Oredsson. "Comparison of three cytotoxicity tests in the evaluation of the cytotoxicity of a spermine analogue on human breast cancer cell lines." Toxicology in vitro 19.3 (2005): 379-387. (Year: 2005).*
Allee et al. "Some effects of social organization on growth in the green sunfish, *Lepomis cyanellus*" Journal of Experimental Zoology 108.1 (1948): 1-19.
Blanckenhorn, Wolf U. "Group size and the cost of agonistic behavior in pumpkinseed sunfish." Ethology ecology & evolution 4.3 (1992): 255-271.

(Continued)

*Primary Examiner* — Robert J Yamasaki
(74) *Attorney, Agent, or Firm* — Nguyen Tarbet LLC (57) ABSTRACT

Methods for identifying animals that are genetically superior, drugs, nutritional strategies, or physiological manipulations that improve feed efficiency or productivity of animals, e.g., selecting animals that are genetically superior for feed efficiency or productivity based on metabolic rates of particular tissues, wherein metabolic rates of certain tissues such as skeletal muscle are inversely proportional to feed efficiency, while metabolic rates of other tissues such as mammary gland are directly proportional to milk production. Thus, animals with low skeletal muscle metabolic rates are generally more feed efficient, e.g., gain more weight per unit of food. The methods herein may be used to improve the genetics, nutrition, and handling or animals more efficiently produced animal products, e.g., meat production, milk, production, egg production, wool production, etc. The methods herein may also be used to determine estimated breeding values of animals for feed efficiency, growth, or production.

5 Claims, 5 Drawing Sheets

(56) References Cited

OTHER PUBLICATIONS

Brand et al. "Evolution of energy metabolism. Proton permeability of the inner membrane of liver mitochondria is greater in a mammal than in a reptile." Biochemical Journal 275.1 (1991): 81-86.
Brown, Margaret E. "The growth of brown trout (*Salmo trutta* Linn.) I. Factors influencing the growth of trout fry." Journal of Experimental Biology 22.3-4 (1946): 118-129.
Clarke et al., "Scaling of metabolic rate with body mass and temperature in teleost fish." Journal of animal ecology 68.5 (1999): 893-905.
Conceição, L. E. C et al., "Cost of growth in larval and juvenile African catfish (*Clarias gariepinus*) in relation to growth rate, food intake and oxygen consumption." Aquaculture 161.1-4 (1998): 95-106.
Cook et al., "Effect of food deprivation on oxygen consumption and body composition of growth-enhanced transgenic Atlantic salmon (*Salmo salar*)." Aquaculture 188.1-2 (2000): 47-63.
Cutts et al. "Aggression and growth depression in juvenile Atlantic salmon: the consequences of individual variation in standard metabolic rate." Journal of Fish Biology 52.5 (1998): 1026-1037 entire document, especially abstract; p. 1027-1029 and p. 1035.
Gjedrem, T. "Genetic improvement of cold-water fish species." Aquaculture research 31.1 (2000): 25-33.
Gadagkar, Sudhindra R. "Social behaviour and growth rate variation in cultivated tilapia (*Oreochromis niloticus*)." (1997).
El-Greisy et al., "Monosex production of tilapia, *Oreochromis niloticus* using different doses of 17α-methyltestosterone with respect to the degree of sex stability after one year of treatment." The Egyptian Journal of Aquatic Research 38.1 (2012): 59-66.
Gjerde, Bjarne. "Growth and reproduction in fish and shellfish." Aquaculture 57.1-4 (1986): 37-55.
Grant, "Aggressiveness and the Foraging Behavior of Yung-of-the-Year Brook Charr (*Salvelinus fontinalis*)" Canadian Journal of Fisheries and Aquatic Sciences, 1990. 47(5): p. 915-920.
Green B.S., Maternal Effects in Fish Populations, Advances in Marine Biology, vol. 54 (2008).
Heath et al., Maternal Effects on Offspring Size: Variation Through Early Development of Chinook Salmon Evolution, vol. 53, No. 5 (Oct. 1999), pp. 1605-1611.
Huang et al., "Response to mass selection for growth rate in Oreochromis niloticus." Aquaculture 85.1-4 (1990): 199-205.
Hulata et al., "Mass selection for growth rate in the Nile tilapia (*Oreochromis niloticus*)." Aquaculture 57.1-4 (1986): 177-184.
Huntingford, F. A., et al. "Social dominance and body size in Atlantic salmon parr, *Salmo solar* L." Journal of Fish Biology 36.6 (1990): 877-881.
Koebele, Bruce P. "Growth and the size hierarchy effect: an experimental assessment of three proposed mechanisms; activity differences, disproportional food acquisition, physiological stress." Environmental Biology of Fishes 12.3 (1985): 181-188.
Livingston, Robert J. "A volumetric respirometer for long-term studies of small aquatic animals." Journal of the Marine Biological Association of the United Kingdom 48.2 (1968): 485-497.
Magnuson, John J. "An analysis of aggressive behavior, growth, and competition for food and space in medaka (*Oryzias latipes* (Pisces, Cyprinodontidae))." Canadian Journal of Zoology 40.2 (1962): 313-363.
Mauger et al., "Cryobanking offish somatic cells: optimizations of fin explant culture and fin cell cryopreservation." Comparative Biochemistry and Physiology Part B: Biochemistry and Molecular Biology 144.1 (2006): 29-37.
McCarthy et al., "The effect of feeding hierarchy on individual variability in daily feeding of rainbow trout, *Oncorhynchus mykiss* (Walbaum)." Journal of Fish Biology 41.2 (1992): 257-263.
Miyashima, et al. "Relationship between oxygen consumption, growth and survival of larval fish." Aquaculture Research 43.5 (2012): 679-687.
Palada-De Vera, M.S. and A.E. Eknath. Predictability of individual growth rates in tilapia, in Proceedings of the fourth International Symposium on Genetics in Aquaculture. 1993. Wuhan, Hubei Province, China: Elsevier.
Purdom "Variation in Fish" in Sea Fisheries Research, F.R.H. Jones, Editor. 1974, Elek Science: London, p. 347-355.
Rampersad et al. "Multiple applications of Alamar Blue as an indicator of metabolic function and cellular health in cell viability bioassays." Sensors 12.9 (2012): 12347-12360. entire document, especially abstract; p. 12350, p. 12351 and p. 12354.
Renquist et al. "Development of an assay for high-throughput energy expenditure monitoring in the zebrafish." Zebrafish 10.3 (2013): 343-352.
Seiler et al., "A comparison of aggressive and foraging behaviour between juvenile cutthroat trout, rainbow trout and F1 hybrids." Animal Behaviour 74.6 (2007): 1805-1812.
Smith et al., "Protein synthesis and oxygen consumption in fish cells." Journal of Comparative Physiology B 165.2 (1995): 93-101.
Tave et al., "Predicted response to selection for early growth in Tilapia nilotica." Transactions of the American Fisheries Society 109.4 (1980): 439-445.
Thodesen et al. "Genetic improvement of tilapias in China: genetic parameters and selection responses in growth of Nile tilapia (*Oreochromis niloticus*) after six generations of multi-trait selection for growth and fillet yield." Aquaculture 322 (2011): 51-64.
Van Meter, David E. "Needle biopsy procedure for electrophoresis in fishes." The Progressive Fish-Culturist 57.2 (1995): 166-167.
Williams, S.Y. and B.J. Renquist, High Throughput Danio Rerio Energy Expenditure Assay. Journal of Visualized Experiments, Issue 107, https://www.jove.com/video/53297, Jan. 2016.
Wohlfarth, G. W. "Shoot carp." Bamidgeh 29.2 (1977): 35-56.
Liu et al. Combination of Entner-Doudoroff Pathway With MEP Increases Isoprene Production In Engineered *Escherichia coli*, PLoS One, 2013, vol. 8, No. 12, e83290, pp. 1-7.
International Search Report Issued for PCT Application No. PCT/US18/61349 dated Jan. 29, 2019.
European Search Report issued for EP Application No. 16839933.5 dated Dec. 5, 2018.
Jordan Rosenfeld et al: "Relationship between growth and standard metabolic rate measurement artefacts and implications for habitat use and life-history adaptation in salmonids", Journal of Animal Ecology, vol. 84, No. 1,Aug. 4, 2014, pp. 4-20.
Donald Reid et al: "The performance advantage of a high resting metabolic rate in juvenile salmon is habitat dependent: RMR, dominance, habitat and growth in salmon", Journal of Animal Ecology, vol. 81, No. 4, Jul. 1, 2012, pp. 868-875.
Tian J. et al., Oral Treatment with gamma-Aminobutyric Acid Improves Glucose Tolerance and Insulin Sensitivity by Inhibiting Inflammation in High Fat Diet-Fed Mice, PLOS One, Sep. 22, 2011, vol. 29, issue 24, United States of America.
Coscina et al. GABA and feeding: Reversal of overeating by central GABA-transaminase inhibition11 , Progress in Neuro-Psychopharmacology & Biological Psychiatry, Elsevier, GB, vol. 7, No. 4-6, Jan. 1, 1983 (Jan. 1, 1983).
Rotiroti D et al: Evidence that a GABAergic mechanism influences the development of DOCA-salt hypertension in the rat11 , European Journal of Pharmacology, Elsevier Sci ence, NL, vol. 83, No. 1-2, Sep. 10, 1982 (Sep. 10, 1982).
Squadrito F et al: A Decreased Brainstem Content of GABA Mediates Hyperinsulinemia in Obese Zucker Rats11 , Neuroscience Research Communications, Wiley, Chichester, GB, vol. 8, No. 1, Jan. 1, 1991 (Jan. 1, 1991).
Kathirvel Elango et al: Betaine improves nonalcoholic fatty liver and associated hepatic insulin resistance: a potential mechanism for hepatoprotection by betaine, American Journal of Physiology—Gastrointestinal and Liver Physiology, vol. 299, No. 5, Nov. 1, 2010 (Nov. 1, 2010).
Renquist B: "Progress Report: Metabolic Rate Assay to Predict Growth Rate of Aquaculture Species 1 Part I: Project Title: Efficient, Rapid Assay for Predicting the Growth Rate of Aquaculture Species Based on Metabolic Rate of the Fertilized Egg Report Given in Year 2014", Jan. 1, 2014 (Jan. 1, 2014).
Minuk G. Y., Gamma-aminobutyric-acid and the liver, Digestive Diseases, Feb. 1993, pp. 45-54, vol. 11, Canada.

(56) References Cited

OTHER PUBLICATIONS

Borra et al. "A simple method to measure cell viability in proliferation and cytotoxicity assays." Brazilian oral research 23.3 (2009): 255-262.
Allee, W.C., et al., Some effects of social organization on growth in the green sunfish, Lepomis cyanellus. Journal of Experimental Zoology, 1948. 108(1): p. 1-19.
Blanckenhorn, W.U., Group size and the cost of agonistic behavior in pumpkinseed sunfish. Ethology Ecology & Evolution, 1992.4(3): p. 255-271.
Brand, M.D., et al., Evolution of energy metabolism. Proton permeability of the inner membrane of liver mitochondria s greater in a mammal than in a reptile. Biochem J, 1991.275 ( Pt 1): p. 81-6.
Brown, M.E., The Growth of Brown trout (Salmo trutta Linn.): I. Factors Influencing the Growth of Trout Fry. Journal of Experimental Biology, 1946. 22(3-4): p. 118-129.
Clarke, A. and N.M. Johnston, Scaling of metabolic rate with body mass and temperature in teleost fish. Journal of Animal Ecology, 1999. 68(5): p. 893-905.
Conceicao, L.E.C., Y. Dersjant-Li, and J.A.J. Verreth, Cost of growth in larval and juvenile African catfish (Clarias gariepinus) in relation to growth rate, food intake and oxygen consumption. Aquaculture, 1998. 161(1-4): p. 95-106.
Cook, J.T., A.M. Sutterlin, and M.A. Mcniven, Effect of food deprivation on oxygen consumption and body composition of growth-enhanced transgenic Atlantic salmon (Salmo salar). Aquaculture, 2000 188(1-2): p. 47-63.
El-Greisy, Z.A. and A.E. El-Gamal, Monosex production of tilapia, Oreochromis niloticus using different doses of 17α-methyltestosterone with respect to the degree of sex stability after one year of treatment. The Egyptian Journal of Aquatic Research, 2012. 38(1): p. 59-66.
Gadagkar, S.R., Social behaviour and growth rate variation in cultivated tilapia (Oreochromis niloticus). 1997, Dalhousie University: Dalhousie University.
Gjedrem, T., Genetic improvement of cold-water fish species. Aquaculture Research, 2000. 31(1): p. 25-33.
Gjerde, B., Growth and Reproduction in Fish and Shellfish. Aquaculture, 1986. 57(1-4): p. 37-55.
Grant, J.W.A., Aggressiveness and the Foraging Behaviour of Young-of-the-Year Brook Charr (Salvelinus fontinalis). Canadian Journal of Fisheries and Aquatic Sciences, 1990. 47(5): p. 915-920.
Huang, C.M. and I.C. Liao, Response to Mass Selection for Growth-Rate in Oreochromis-Niloticus. Aquaculture, 1990. 85(1-4): p. 199-205.
Hulata, G., G.W. Wohlfarth, and A. Halevy, Mass Selection for Growth-Rate in the Nile Tilapia (Oreochromis-niloticus). Aquaculture, 1986 57(1-4): p. 177-184.

Huntingford, F.A., et al., Social dominance and body size in Atlantic salmon parr, Salmo solar L. Journal of Fish Biology, 1990. 36(6): p. 877-881.
Koebele, B., Growth and the size hierarchy effect: an experimental assessment of three proposed mechanisms; activity differences, disproportional food acquisition, physiological stress. Environmental Biology of Fishes, 1985. 12(3) p. 181-188.
Livingston, R.J., A volumetric respirometer for long-term studies of small aquatic animals. Journal of the Marine Biological Association of the United Kingdom, 1968. 48: p. 485-497.
Magnuson, J.J., An Analysis of Aggressive Behavior, Growth, and Competition for Food and Space in Medaka (Oryzias latipes (Pisces, Cyprinodontidae)). Canadian Journal of Zoology, 1962. 40 (2): p. 313-363.
Mauger, R.E., P.Y. Le Bail, and C. Labbe, Cryobanking offish somatic cells: Optimizations of fin explant culture and fin cell cryopreservation. Comparative Biochemistry and Physiology B—Biochemistry & Molecular Biology, 2006. 144(1): p. 29-37.
McCarthy, I.D., C.G. Carter, and D.F. Houlihan, The effect of feeding hierarchy on individual variability in daily feeding of rainbow trout, Oncorhynchus mykiss (Walbaum). Journal of Fish Biology, 1992. 41(2): p. 257-263.
Miyashima, A., et al., Relationship between oxygen consumption, growth and survival of larval fish. Aquaculture Research, 2012. 43(5): p. 679-687.
Purdom, C.E., Variation in Fish, in Sea Fisheries Research, F.R.H. Jones, Editor. 1974, Elek Science: London, p. 347-355.
Renquist, B.J., et al., Development of an assay for high-throughput energy expenditure monitoring in the zebrafish. Zebrafish, 2013. 10(3): p. 343-52.
Seiler, S.M. and E.R. Keeley, A comparison of aggressive and foraging behaviour between juvenile cutthroat trout, rainbow trout and F1 hybrids. Animal Behaviour, 2007. 74(6): p. 1805-1812.
Smith, R.W. and D.F. Houlihan, Protein synthesis and oxygen consumption in fish cells. Journal of Comparative Physiology B, 1995. 165(2): p. 93-101.
Tave, D. and R.O. Smitherman, Predicted Response to Selection for Early Growth in Tilapia-Nilotica. Transactions of the American Fisheries Society, 1980. 109(4): p. 439-445.
Thodesen, J., et al., Genetic improvement of tilapias in China: Genetic parameters and selection responses in growth of Nile tilapia (Oreochromis niloticus) after six generations of multi-trait selection for growth and fillet yield. Aquaculture, 2011. 322: p. 51-64.
Vanmeter, D.E., Needle-Biopsy Procedure for Electrophoresis in Fishes. Progressive Fish-Culturist, 1995. 57(2): p. 166-167.
Wohlfarth, G.W., Shoot carp. Bamidgeh, 1977.29(2): p. 35-56.

* cited by examiner

METHODS FOR MEASURING REDUCING EQUIVALENT PRODUCTION BY TISSUES TO DETERMINE METABOLIC RATES AND METHODS OF USE

CROSS-REFERENCES TO RELATED APPLICATIONS

This application is a continuation-in-part and claims benefit of PCT Patent Application No. PCT/US18/61349, filed Nov. 15, 2018, which claims benefit of U.S. Provisional Patent Application No. 62/586,578, filed Nov. 15, 2017 and claims benefit of U.S. patent application Ser. No. 15/754,126, filed Feb. 21, 2018, the specification(s) of which is/are incorporated herein in their entirety by reference.

This application is also a continuation-in-part and claims benefit of U.S. patent application Ser. No. 15/754,126, filed Feb. 21, 2018, which is 371 application and claims benefit of PCT/US16/48006, filed Aug. 22, 2016, which claims benefit of U.S. Provisional Patent Application No. 62/208,433, filed Aug. 21, 2015, the specification(s) of which is/are incorporated herein in their entirety by reference.

GOVERNMENT SUPPORT

This invention was made with government support under Grant Nos. 2010-38500-21758, 2015-70007-24236, and 2016-67016-24866, awarded by USDA/NIFA. The government has certain rights in the invention.

FIELD OF THE INVENTION

The present invention relates to the use of measuring reducing equivalents, such as NADH, $FADH_2$, NADP(H), and/or Coenzyme Q, to measure tissue metabolic rate in animals and humans. The methods of measuring reducing equivalents provide a high throughput means of determining metabolic rates of animals or humans. The methods may be used for a variety of purposes, for example assessing feed efficiency, assessing productivity of animals, determining a likelihood of developing obesity, sorting animals, etc.

BACKGROUND OF THE INVENTION

Basal metabolic rate may be estimated by housing animals in metabolic chambers, but the use of metabolic chambers is difficult due to practical and economic challenges. Alternatively, one could measure ex vivo metabolic rate of tissues using an oxygen sensor or by measuring $CO_2$ acidification of the media. However, neither of these measures have the sensitivity associated with the accumulation of signal noted with this invention, and both are subject to exchange of gases between the media and the air.

The technique described herein was previously used to assess cell viability, not metabolic rate. Thus, it was surprising to discover that measuring reducing equivalents in tissues of an animal (or human) could be used as a proxy for measuring the metabolic rate of the animal (or human). An additional leap was made when it was discovered that tissue metabolic rate could be applied to assess an individual's feed efficiency or a tissue's production potential. The methods of the present invention feature measuring reducing equivalents (e.g., NADH, $FADH_2$, NADP(H), Coenzyme Q, etc.), which are used to determine the metabolic rate of the animal or human (e.g., tissue-specific metabolic rate). The present invention provides a high throughput means of determining metabolic rate of an animal or human.

The present invention also features the use of said methods, e.g., the methods for measuring metabolic rates using reducing equivalent measurements. For example, the methods herein may be used to:

Identify and/or select feed efficient animals;
Eliminate animals with poor feed efficiency;
Identify and/or select high producing animals (e.g., high milk production, high egg production, meat production, or any other appropriate animal product);
Identify animals or subjects (e.g., humans) that are more likely to become overweight or obese;
Identify animals or subjects (e.g., humans) that are more resistant to obesity;
Develop an estimated breeding value for feed efficiency, growth, milk production, or egg production in animals;
Select breeding animals with higher production or better feed efficiency;
Identify animals or humans with a particular likelihood of developing obesity;
Test for metabolic rate responses to a drug (e.g., antibiotic), nutrient, or other molecule. Given the relationship with feed efficiency and production, these tests could be applied to assess the effect of this stimulus on production, feed efficiency, and obesigenic drive;
Evaluate the effect of a stress or stimulus (e.g., exercise) on metabolic rate of animals. Given the relationship with feed efficiency and production, these tests could be applied to assess the effect of this stimulus on production, feed efficiency, and obesigenic drive.

Without wishing to limit the present invention to any theory or mechanism, it is believed that the technology of the present invention is advantageous because it provides a fast, high-throughput, scalable and easy means of assessing metabolic rate of tissues (via cell viability assays, e.g., measuring reducing equivalents), while allowing the user to associate that metabolic rate to parameters such as feed efficiency and tissue-specific production formation. For example, by applying this in skeletal muscle of young animals, one can assess growth; by applying this in adult skeletal muscle, one can measure or assess feed efficiency; by applying this to lactating mammary glands, one can asses milk production.

SUMMARY OF THE INVENTION

As previously discussed, the present invention features methods of measuring reducing equivalents (e.g., NADH, $FADH_2$, Coenzyme Q, etc.) in a tissue of an animal (or human) to determine the metabolic rate of the animal (or human) (or a tissue-specific metabolic rate). The present invention is not limited to any particular method for measuring reducing equivalents. For example, the present invention is not limited to the use of resazurin, MTT, or any other particular reducing equivalent indicator. In some embodiments, measuring reducing equivalents may feature measuring NADH production. In some embodiments, measuring reducing equivalents may feature measuring $FADH_2$ production. In some embodiments, measuring reducing equivalents may feature measuring Coenzyme Q. In some embodiments, measuring reducing equivalents may feature measuring a combination of NADH, $FADH_2$, NADP(H), or Coenzyme Q.

As used herein, the term "animal" may refer to any appropriate animal or human, e.g., cattle (e.g., dairy cattle, beef cattle), goats, sheep, swine, mice, dogs, cats, humans, non-human primates, chickens, fish, mollusks, etc. For example, in humans, non-human primates, dogs, cats, etc., the methods of the present invention may be used to determine a likelihood of obesity. The methods and systems of the present invention are not limited to the animals disclosed herein.

As used herein, the term "tissue" may refer to any appropriate tissue of the animal or human, e.g., skeletal muscle, mammary tissue, brown adipose tissue, white adipose tissue, liver, kidney, fin, etc. The methods and systems of the present invention are not limited to the tissues disclosed herein.

Without wishing to limit the present invention to any theory or mechanism, a lower tissue-specific metabolic rate can be indicative of a lower whole animal basal metabolic rate (energy expended to maintain proper tissue function without a change in tissue mass) if that tissue mass is large relative to whole body mass (e.g. skeletal muscle). A lower basal metabolic rate allows for less of the dietary energy to go toward body maintenance energy requirements and more to go toward growth or product (e.g., milk, eggs, meat, etc.) formation. Thereby, a low skeletal muscle metabolic rate in slow/non-growing adult animals is indicative of the potential for good feed efficiency (product mass/feed mass), and a high potential for product (e.g., milk, meat) production, etc.

The present invention also features the use of the methods of measuring reducing equivalents for determining metabolic rates of animals (or humans).

For example, the present invention provides methods of identifying animals with a particular feed efficiency, e.g., a high feed efficiency. As used herein, the term "feed efficiency" refers to the amount of weight gained per unit of feed or product produced per unit feed. The present invention also features methods of stratifying animals based on feed efficiency. The present invention also features method of selection (e.g., methods of grouping, sequestering, etc.) of animals with a particular feed efficiency, e.g., a high feed efficiency. In some embodiments, feed efficiency determined by the methods herein may be used to calculate an expected progeny difference.

The aforementioned methods (e.g., methods of identifying animals with a particular feed efficiency, etc.) and other methods described herein may comprise determining the reducing equivalent production (e.g., an amount, a change in, etc.) in a tissue sample (e.g., skeletal muscle tissue sample) from the animal, wherein the reducing equivalent production (e.g., an amount, a change in, etc.) in the tissue sample is inversely related to feed efficiency. In some embodiments, if the reducing equivalent production (e.g., an amount, a change in, etc.) in the skeletal muscle tissue sample is below a predetermined threshold, then the animal from which the skeletal muscle tissue sample was obtained has a high feed efficiency compared to animals having a reducing equivalent production (e.g., an amount, a change in, etc.) above the predetermined threshold. Determining the reducing equivalent production (e.g., an amount, a change in, etc.) in the tissue sample may comprise introducing a reducing equivalent indicator to the tissue sample and measuring an amount of or a change in reducing equivalent indicator (which is indicative of metabolic activity).

The predetermined threshold may be an average of reducing equivalent production for a breed, herd, or species of the animal. The predetermined threshold may be determined by the user, e.g., based on a desired stringency of selection for feed efficiency. The predetermined threshold may be a percentile level (e.g., $5^{th}$ percentile, $10^{th}$ percentile, $25^{th}$ percentile, $50^{th}$ percentile, etc.). The predetermined threshold may be determined using a cohort of animals with a known reducing equivalent production (e.g., an amount, a change in, etc.) and known feed efficiencies. The predetermined threshold may stratify animals by feed efficiency.

With respect to the methods described herein, in some embodiments, the reducing equivalent is NADH. In some embodiments, the reducing equivalent is NADP(H). In some embodiments, the reducing equivalent is $FADH_2$. In some embodiments, the reducing equivalent is Coenzyme Q. In some embodiments, the reducing equivalent is NADH or $FADH_2$. In some embodiments, the reducing equivalent is NADH or Coenzyme Q. In some embodiments, the reducing equivalent is $FADH_2$ or Coenzyme Q. In some embodiments, the reducing equivalent is NADH or NADP(H). In some embodiments, the reducing equivalent is NADP(H) or CoEnzyme Q. In some embodiments, the reducing equivalent is NADP(H) or $FADH_2$. In some embodiments, the reducing equivalent is one or more of: NADH, $FADH_2$, NADP(H), and Coenzyme Q. In some embodiments, the reducing equivalent is NADH, $FADH_2$, or Coenzyme Q. In some embodiments, the reducing equivalent is NADH, $FADH_2$, NADP(H), or Coenzyme Q.

The method may further comprise using the animal identified as having high feed efficiency for breeding. The method may further comprise using the animal identified as having high feed efficiency for production of an animal product (e.g., milk, meat, etc.).

The present invention also provides methods of identifying animals with a particular milk production, e.g., high milk production. The present invention also features methods of stratifying animals based on milk production. The present invention also features method of selection (e.g., methods of grouping, sequestering, etc.) of animals with a particular milk production, e.g., a high milk production.

The aforementioned methods (e.g., methods of identifying animals with a high milk production, etc.) and other methods described herein may comprise determining reducing equivalent production (e.g., an amount, a change in, etc.) in a mammary tissue sample from the animal, wherein the reducing equivalent production (e.g., an amount, a change in, etc.) in the mammary tissue sample is directly related to potential for milk production. In some embodiments, if the reducing equivalent production (e.g., an amount, a change in, etc.) in the mammary tissue sample is above a predetermined threshold, then the animal from which the mammary tissue sample was obtained has a high milk production potential compared to animals having a reducing equivalent production (e.g., an amount, a change in, etc.) below the predetermined threshold. Determining the reducing equivalent production in the tissue sample may comprise introducing a reducing equivalent indicator to the tissue sample and measuring an amount of or a change in reducing equivalent indicator (which is indicative of metabolic activity).

The predetermined threshold may be an average of reducing equivalent production for a breed, herd, or species of the animal. The predetermined threshold may be determined by the user, e.g., based on a desired stringency of selection for milk production potential. The predetermined threshold may be a percentile level (e.g., $5^{th}$ percentile, $10^{th}$ percentile, $25^{th}$ percentile, $50^{th}$ percentile, etc.). The predetermined threshold may be determined using a cohort of animals with a known reducing equivalent production (e.g., an amount, a change in, etc.) and known milk production. The predetermined threshold may stratify animals by milk production potential.

With respect to the methods described herein, in some embodiments, the reducing equivalent is NADH. In some embodiments, the reducing equivalent is NADP(H). In some embodiments, the reducing equivalent is $FADH_2$. In some embodiments, the reducing equivalent is Coenzyme Q. In some embodiments, the reducing equivalent is NADH or FADH$_2$. In some embodiments, the reducing equivalent is NADH or Coenzyme Q. In some embodiments, the reducing equivalent is FADH$_2$ or Coenzyme Q. In some embodiments, the reducing equivalent is NADH or NADP(H). In some embodiments, the reducing equivalent is NADP(H) or CoEnzyme Q. In some embodiments, the reducing equivalent is NADP(H) or FADH$_2$. In some embodiments, the reducing equivalent is one or more of: NADH, FADH$_2$, NADP(H), and Coenzyme Q. In some embodiments, the reducing equivalent is NADH, FADH$_2$, or Coenzyme Q. In some embodiments, the reducing equivalent is NADH, FADH$_2$, NADP(H), or Coenzyme Q.

The method may further comprise using the animal identified as having high milk production for breeding. The method may further comprise using the animal identified as having high milk production for production of milk.

The present invention also features methods of calculating a feed efficiency breeding value for an animal. In some embodiments, the method comprises determining a feed efficiency based on metabolic rate of a tissue sample from the animal, e.g., as described herein, e.g., wherein metabolic rate is determined by determining reducing equivalent production (e.g., an amount, a change in, etc.); and assigning an estimated expected progeny difference from the breed average based on the metabolic rate of the tissue sample. In some embodiments, the estimated breeding value indicates the genetics for feed efficiency of the potential brood stock. In some embodiments, the method further comprises combining estimated feed efficiency with one or more additional estimated breeding values, e.g., ribeye area, intramuscular fat, fat depth, birth weight, weaning weight, and carcass yield.

The present invention also features methods of favoring or skewing a genetic makeup of an animal population (e.g., a newborn animal population) towards having a high feed efficiency. In some embodiments, the method comprises determining a metabolic rate of a tissue sample (e.g., skeletal muscle tissue) from the animals (as described herein). In some embodiments, the method further comprises selecting the animals with the best feed efficiency for breeding a newborn animal population with a particular predicted feed efficiency.

The present invention also features methods of favoring or skewing a genetic makeup of an animal population (e.g., a newborn animal population) towards having high milk production. In some embodiments, the method comprises determining a metabolic rate of a tissue sample (e.g., mammary tissue) from the animals (as described herein). In some embodiments, the method further comprises selecting the animals with the best milk production for breeding a newborn animal population with a particular predicted milk production.

The present invention also features methods for detecting an effect of a drug, dietary supplement, diet, or other composition on feed efficiency of an animal. In some embodiments, the method comprises determining a baseline tissue-specific metabolic rate for the animal by measuring reducing equivalent production (e.g., an amount, a change in, etc.) in a first tissue sample (e.g., skeletal muscle) from the animal; administering the drug, dietary supplement, diet, or other composition to the animal; then determining the reducing equivalent production in a second tissue sample of the tissue of the animal (a second tissue-specific metabolic rate). In some embodiments, if the second tissue-specific metabolic rate is equal to the baseline tissue-specific metabolic rate, then the drug, dietary supplement, diet, or other composition does not affect feed efficiency of the animal. In some embodiments, if the second tissue-specific metabolic rate is less than the baseline tissue-specific metabolic rate then the drug, dietary supplement, diet, or other composition has a positive effect on feed efficiency of the animal. In some embodiments, if the second tissue-specific metabolic rate is greater than the baseline tissue-specific metabolic then the drug, dietary supplement, diet, or other composition has a negative effect on feed efficiency of the animal.

In some embodiments, the method comprises administering the drug, dietary supplement, diet, or composition to the animal; and determining a metabolic rate for the animal by determining reducing equivalent production (e.g., an amount, a change in, etc.) in a tissue (e.g., skeletal muscle) of the animal. In some embodiments, if the metabolic rate of the animal is equal to a control metabolic rate, the control metabolic rate being a metabolic rate of one or a group animals not administered the drug, dietary supplement, diet, or other composition, then the drug, dietary supplement, diet, or other composition does not affect feed efficiency of the animal. In some embodiments, if the metabolic rate of the animal is less than a control metabolic rate, the control metabolic rate being a metabolic rate of one or a group animals not administered the drug, dietary supplement, diet, or other composition, then the drug, dietary supplement, diet, or other composition has a positive affect on feed efficiency of the animal. In some embodiments, if the metabolic rate of the animal is greater than a control metabolic rate, the control metabolic rate being a metabolic rate of one or a group animals not administered the drug, dietary supplement, diet, or other composition, then the drug, dietary supplement, diet, or other composition has a negative effect on feed efficiency of the animal.

The present invention also features methods of detecting an effect of a drug, dietary supplement, diet, or other composition on milk production of an animal. In some embodiments, the method comprises determining a baseline tissue-specific metabolic rate for the animal by measuring reducing equivalent production (e.g., an amount, a change in, etc.) in a first tissue sample of a mammary tissue of the animal; administering the drug, dietary supplement, diet, or other composition to the animal; and determining a second tissue-specific metabolic rate for the animal by measuring reducing equivalent production (e.g., an amount, a change in, etc.) in a second tissue sample of the mammary tissue of the animal. In some embodiments, if the second tissue-specific metabolic rate is equal to the baseline tissue-specific metabolic rate, then the drug, dietary supplement, diet, or other composition does not affect milk production of the animal. In some embodiments, if the second tissue-specific metabolic rate is less than the baseline tissue-specific metabolic then the drug, dietary supplement, diet, or other composition has a negative effect on milk production of the animal. In some embodiments, if the second tissue-specific metabolic rate is greater than the baseline tissue-specific metabolic then the drug, dietary supplement, diet, or other composition has a positive effect on milk production of the animal.

In some embodiments, the method comprises administering the drug, dietary supplement, diet, or composition to the animal; and determining a tissue-specific metabolic rate for the animal by determining reducing equivalent production (e.g., an amount, a change in, etc.) in a mammary tissue of the animal. In some embodiments, if the tissue-specific metabolic rate of the animal is equal to a control tissue-specific metabolic rate, the control tissue-specific metabolic rate being a metabolic rate of mammary tissue of one or a group animals not administered the drug, dietary supplement, diet, or other composition, then the drug, dietary supplement, diet, or other composition does not affect milk production of the animal. In some embodiments, wherein if the tissue-specific metabolic rate of the animal is less than a control tissue-specific metabolic rate, the control tissue-specific metabolic rate being a metabolic rate of one or a group animals not administered the drug, dietary supplement, diet, or other composition, then the drug, dietary supplement, diet, or other composition has a positive affect on milk production of the animal. In some embodiments, wherein if the tissue-specific metabolic rate of the animal is greater than a control tissue-specific metabolic rate, the control tissue-specific metabolic rate being a metabolic rate of one or a group animals not administered the drug, dietary supplement, diet, or other composition, then the drug, dietary supplement, diet, or other composition has a negative effect on milk production of the animal.

The present invention also features methods of testing a drug, dietary supplement, diet, or composition ex vivo. The method may feature obtaining samples from the animal and treating the samples with the drug, dietary supplement, diet, or composition in culture to determined wither or not there is an affect of the drug, dietary supplement, diet, or composition on the production of reducing equivalents (e.g., metabolic rate).

As used herein, the term "baseline," referring to metabolic rate or other parameter, may refer to an amount predetermined by the industry or by the user. For example, the baseline may be predetermined by the user by testing the animal's metabolic rate (or milk production) prior to administration of the drug or composition. In some embodiments, the baseline is predetermined by other individuals, e.g., national averages, breed averages, etc.

The present invention also features methods for treating animals to improve milk production. The method may comprise determining an amount of a drug, dietary supplement, diet, or other composition to administer to achieve a particular milk production (e.g., using the methods or a combination of methods described herein), and administering the dose of the drug, dietary supplement, diet, or other composition to achieve the desired milk production.

The present invention also features methods for treating animals to improve feed efficiency. The method may comprise determining an amount of a drug, dietary supplement, diet, or other composition to administer to achieve a particular feed efficiency (e.g., using the methods or a combination of methods described herein), and administering the dose of the drug, dietary supplement, diet, or other composition to achieve the desired feed efficiency.

As used herein, the terms percentile, percentile level, threshold, threshold level, and/or baseline may refer to a predetermined amount or level that is determined by the user or by the industry. For example, in some embodiments, the threshold level or percentile level is an industry average. In some embodiments, the threshold level or percentile level is set by the user. The threshold level may be unique to a particular breed or herd. The threshold level or percentile level may depend on the desired feed efficiency, milk production, etc.

In some embodiments, the threshold or percentile is the $50^{th}$ percentile or average. In some embodiments, the threshold or percentile is the $5^{th}$ percentile. In some embodiments, the threshold or percentile is the $10^{th}$ percentile. In some embodiments, the threshold or percentile is the $15^{th}$ percentile. In some embodiments, the threshold or percentile is the $20^{th}$. In some embodiments, the threshold or percentile is the $25^{th}$ percentile. In some embodiments, the threshold or percentile is the $30^{th}$ percentile. In some embodiments, the threshold or percentile is the $35^{th}$ percentile. In some embodiments, the threshold or percentile is the $40^{th}$ percentile. In some embodiments, the threshold or percentile is the $45^{th}$ percentile. In some embodiments, the threshold or percentile is the $55^{th}$ percentile. In some embodiments, the threshold or percentile is the $60^{th}$ percentile. In some embodiments, the threshold or percentile is the $65^{th}$ percentile. In some embodiments, the threshold or percentile is the $70^{th}$ percentile. In some embodiments, the threshold or percentile is the $75^{th}$ percentile. In some embodiments, the threshold or percentile is the $80^{th}$ percentile. In some embodiments, the threshold or percentile is the $85^{th}$ percentile. In some embodiments, the threshold or percentile is the $90^{th}$ percentile. In some embodiments, the threshold or percentile is the $95^{th}$ percentile. In some embodiments, the threshold or percentile is the $5^{th}$ percentile. In some embodiments, the threshold or percentile is the $99^{th}$ percentile. In some embodiments, the threshold or percentile is the $5^{th}$ percentile.

The present invention is not limited to the aforementioned thresholds or percentiles. The present invention is not limited to the aforementioned means of determining the thresholds or percentiles.

Without wishing to limit the present invention to any theory or mechanism, features and advantages of the methods of the present invention include, but are not limited to: (a) the ability to test tissue-specific metabolic rate; (b) the ability to test for genetic, nutrition, endocrine, and physiological effects on tissue-specific metabolic rate; (c) the ability to test for effects either in vivo or ex vivo; (d) the ability to test the effect on metabolic rate of any water or DMSO soluble compound; (e) the ease of application and measurement (includes fluorescence change or color change, which can be measured from a photograph); (f) the use of a cumulative signal, which is more sensitive that a simple measure of oxygen consumption and allows for differentiation of small differences between animals; (g) the simplicity, including only the mixture of a few solutions; and (h) the ability to scale this up for simultaneous measure of 1000s of samples.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which:

FIG. 4A shows that biopsies from mature fully-grown cows have a lower metabolic rate than those collected from young growing cattle. Variability in FC/4 h induced by skeletal muscle biopsies from young and mature cows is robust. This variability may be important for improving genetics for efficiency.

DETAILED DESCRIPTION OF THE INVENTION

Measuring Metabolic Rate

The present invention provides methods of measuring metabolic rates of animas (or humans), wherein the methods feature measuring reducing equivalents (e.g., NADH, $FADH_2$, NADP(H), Coenzyme Q, etc.). The methods may comprise obtaining a tissue biopsy from the animal (e.g., skeletal muscle tissue biopsy, mammary tissue biopsy, etc.). Biopsies may be obtained by an appropriate means, e.g., using a needle biopsy tool, via crude dissection, etc. The method may comprise putting at least a portion of the biopsy in appropriate media in a plate or dish (e.g., 12-well plate, 24-well plate, 96-well plate, etc.). The biopsy tissue in the dish is then subjected to a reducing equivalent indicator, e.g., a dye. The biopsies are then read, e.g., color (e.g., RGB analysis), absorbance, fluorescence, and/or any other appropriate parameter may be measured to assess change in signal. The measured change is indicative of the degree of reducing equivalent (e.g., NADH, $FADH_2$, NADP(H), Coenzyme Q, etc.) production. Note the concentration of reducing equivalent indicator (e.g., resazurin, MTT, AlamarBlue®, PrestoBlue®) may be titrated to meet specific needs; titration of concentration can alter sensitivity of the assay. The present invention is not limited to the aforementioned reducing equivalent indicators.

As a non-limiting specific example, some studies herein use resazurin assays for measuring NADH $H^+$ production. A biopsy is collected from an animal and immediately put into a well of a 96-well plate containing Dulbecco's Modified Eagle Medium (DMEM) with Pen/Strep and put into a 37° C. incubator with 95% $O_2$ 5% $CO_2$. After 1 h equilibration, biopsies are moved into a well filled with 300 ul DMEM supplemented with 0.1% DMSO, Pen/Strep and 0.16% 10× resazurin. Immediately after moving the tissue biopsies, color (rgb analysis), absorbance (570-600 nm) or fluorescence (excitation 530 nM, emission 590 nM) is measured. The plate is then "read" (color analysis or plate reader measure of absorbance and fluorescence) at intervals to assess change in signal. The measured change in signal is indicative of the degree of NADH H production. The signal accumulates with time.

Figure 1A:
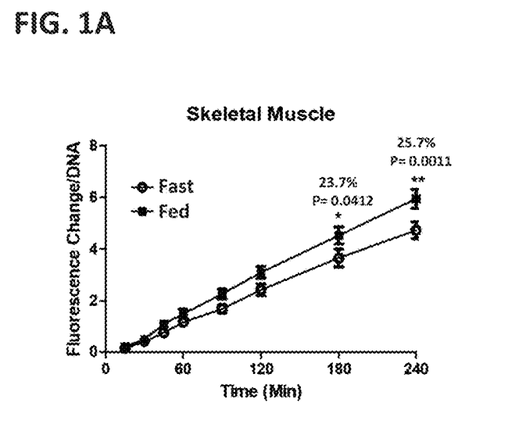
FIG. 1A shows that skeletal muscle biopsies cause a linear increase in fluorescent signal with time indicating that the skeletal muscle tissue continues to produce reducing equivalents and remains viable through the incubation period. Moreover, it is shown that this signal is sensitive to fasting (16 hr fast).
Figure 1B:
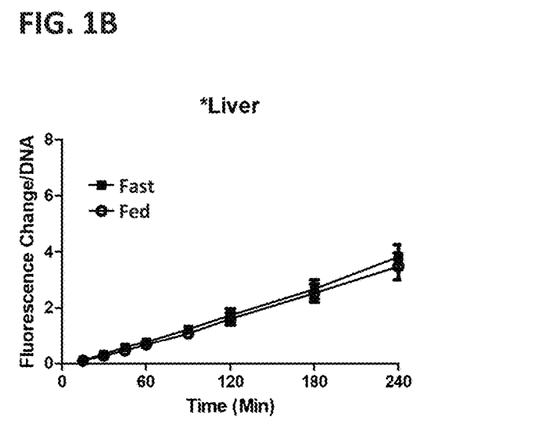
FIG. 1B shows that liver biopsies cause a linear increase in fluorescent signal with time indicating that the liver tissue continues to produce reducing equivalents and remains viable through the incubation period. Moreover, it is shown that this signal is not sensitive to fasting (16 hr fast).
Figure 1C:
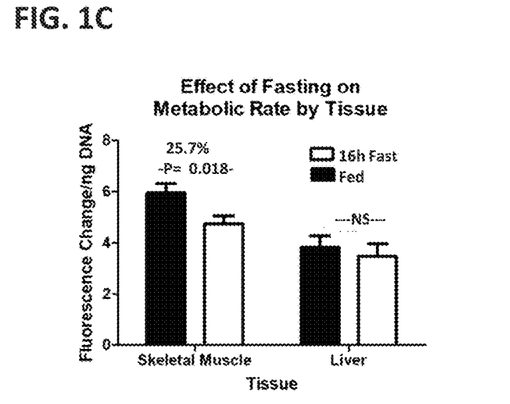
FIG. 1C shows the 4 h metabolic rate from FIGS. 5A and 5B (fluorescence change/ng DNA). Metabolic rate of skeletal muscle biopsies is decreased by fasting (16 h), but fasting did not affect liver biopsy metabolic rate. This establishes that the assay can be applied to assess the effect of nutritional state on tissue specific metabolic rate.
Figure 1D:
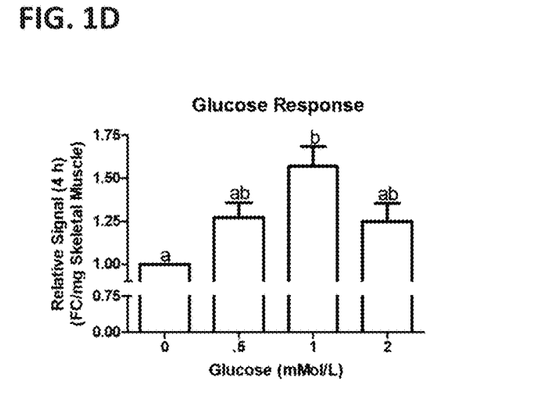
FIG. 1D shows glucose (1 mM) in the media increases skeletal muscle biopsy metabolic rate measured as relative change in fluorescence/mg tissue. This establishes that the assay can be applied to assess the effect of nutrients on tissue specific metabolic rate.
Figure 1E:
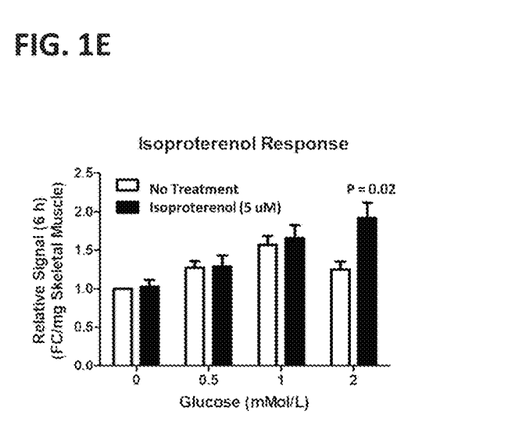
FIG. 1E shows Isoproterenol, a beta-adrenergic receptor agonist, increases skeletal muscle metabolic rate at high glucose concentrations (2 mM). This establishes that the assay can be applied to assess the effect of drugs on tissue specific metabolic rate.
Figure 1F:
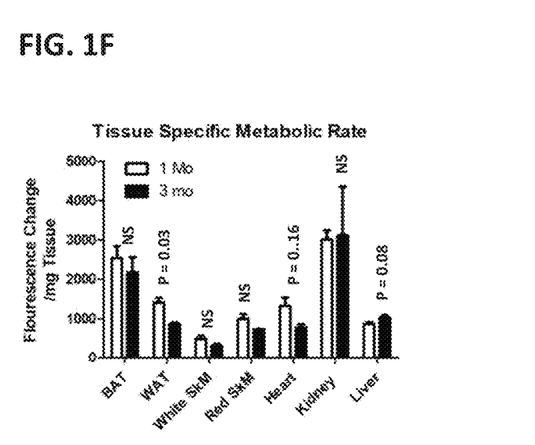
FIG. 1F shows metabolic rates (expressed as fluorescence change/mg tissue) of tissue biopsies (e.g., brown adipose tissue (BAT), white adipose tissue (WAT), white skeletal muscle, red skeletal muscle, heart, kidney, and liver) differ across tissues and with age of the mouse (1 month, 3 months). This establishes the assay can be used to assess the effect of physiological parameters (including, but not limited to age, exercise, hormonal status, etc.) on tissue specific metabolic rate.

FIG. 1A, FIG. 1B, FIG. 1C, FIG. 1D, FIG. 1E, and FIG. 1F show the application of the resazurin-based assay to homeothermic tissue collected from mice. FIG. 1A shows skeletal muscle metabolic rate linearly increases with time to 4 hours and is sensitive to fasting. FIG. 1B shows liver metabolic rate (linearly increases with time and is not sensitive to fasting. FIG. 1C shows metabolic rate (expressed as fluorescence change/ng DNA) is decreased by fasting in skeletal muscle. FIG. 1D shows glucose in the media increases skeletal muscle metabolic rate (sensitive to ex vivo nutrient application). FIG. 1E shows Isoproterenol, a beta-adrenergic receptor agonist, increases skeletal muscle metabolic rate at high glucose concentrations (sensitive to drug application). FIG. 1F shows metabolic rates of tissues differ across tissues and with age of the mouse (1 month, 3 months).

Figure 2:
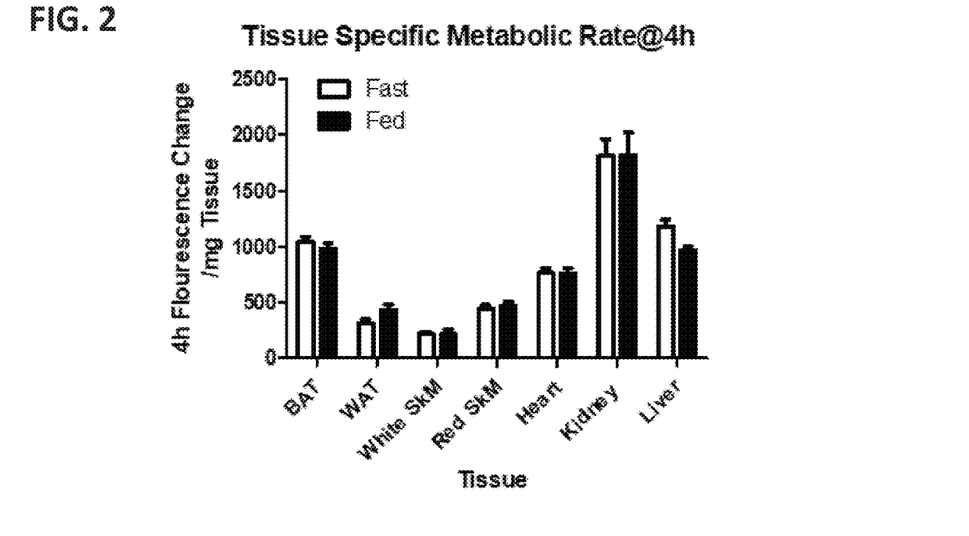
FIG. 2 shows metabolic rates (as changes in fluorescence over time) of many tissues (e.g., brown adipose tissue (BAT), white adipose tissue (WAT), white skeletal muscle, red skeletal muscle, heart, kidney, and liver) in fed and fasted mice. This establishes that the invention described herein can be applied across tissues.

FIG. 2 shows the metabolic rates of various tissues, e.g., brown adipose tissue (BAT), white adipose tissue (WAT), white skeletal muscle, red skeletal muscle, heart, kidney, and liver in fed and fasted mice, showing the effect of a physiological change (fasting) on metabolic rate (as measured by the 4 hr fluorescence change/mg tissue). White adipose tissue and liver were the two tissues that were affected by fasting when measured as the 4 hr fluorescence change per mg tissue. Skeletal muscle tissues were unaffected. Without wishing to limit the present invention to any theory or mechanism, DNA may be a preferred correction factor.

The present invention is not limited to the aforementioned methods and compositions for measuring reducing equivalents.

Feed Efficiency and Productivity

Without wishing to limit the present invention to any theory or mechanism, it is believed that a lower tissue metabolic rate is associated with a higher feed efficiency and/or a higher amount of productivity (e.g., higher production of milk, muscle, eggs, etc.).

The present invention provides methods for identifying (and/or) selecting animals with high feed efficiency. The present invention also provides methods of identifying animals with increased productivity (e.g., egg production, milk production, etc.), methods of predicting animals with high productivity, and methods of selecting animals with high productivity. The methods herein select for lower tissue-specific metabolic rates (e.g., lower skeletal muscle metabolic rates) and/or lower basal metabolic rates, etc.

Other methods provided herein include but are not limited to methods of determining breeding values of animals.

In some embodiments, to determine an animal's feed efficiency, a tissue from an animal (e.g., skeletal muscle) is tested to determine the metabolic rate by determining reducing equivalent production (e.g., an amount, a change in, etc.). As an example, the animal or tissue from the animal (e.g., skeletal muscle) is tested with a reducing equivalent indicator and evaluated by assessing the change in fluorescence, absorbance (570-600 nM when using resazurin), or by color. In some embodiments, the resulting metabolic rate is then compared to the range of known changes in fluorescence, absorbance, or color and a percentile is determined.

In some embodiments, tissue specific changes in fluorescence, absorbance, or color are corrected for DNA, protein, or mass of the sample.

In some embodiments, the reducing equivalents are used in mathematical models may be used in conjunction with the reducing equivalent (metabolic rate) data to determine or predict feed efficiency or productivity, e.g., weight gain, egg production, milk production, etc. In the example of milk production, a prospective study of a cohort of dairy cows may be used to predict high milk production. Mammary tissues may be obtained and tested for metabolic rate, and milk production can be determined for each subject. A candidate scoring function may be chosen to stratify future tested animals into a category of high milk production or low milk production (or other different or additional categories). For example, those animals with high mammary gland metabolic rates may be selected as animals predicted to have high milk production.

In some embodiments, the methods of the present invention feature selection of animals with a low basal metabolic rate (e.g., a low tissue-specific metabolic rate). In some embodiments, the methods of the present invention feature selection of animals with a high basal metabolic rate (e.g., a high tissue-specific metabolic rate).

Figure 3:
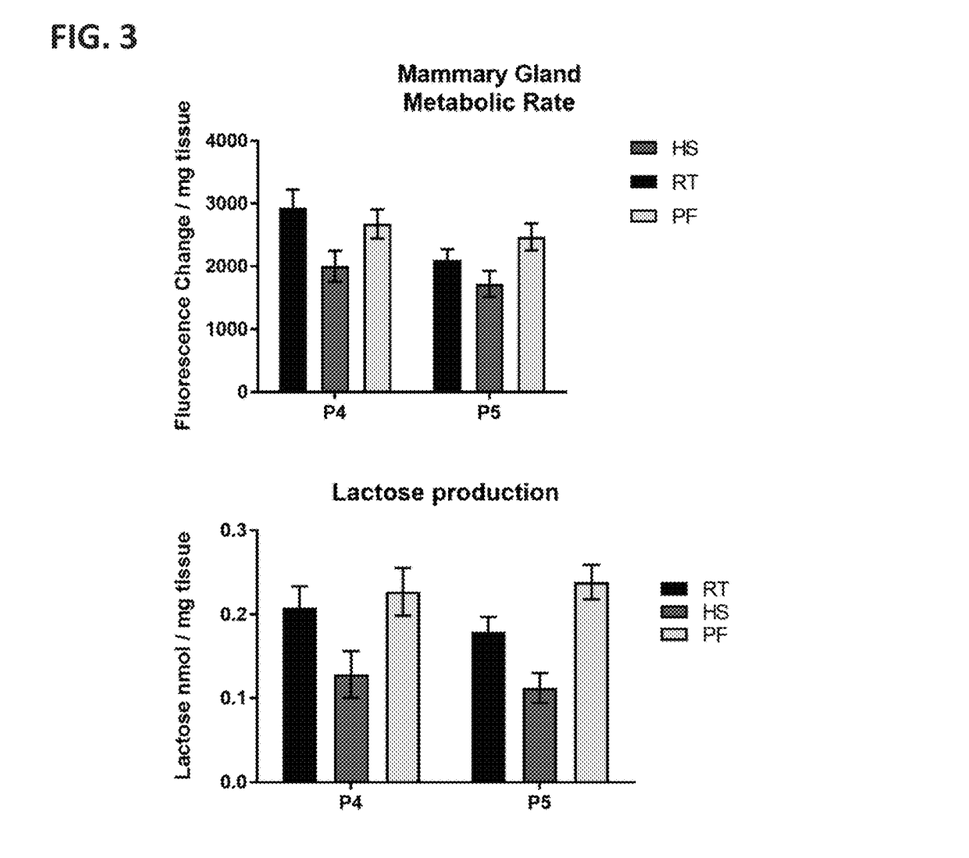
FIG. 3 shows that mammary gland biopsy metabolic rate may be used to predict milk production. Ex vivo mammary gland metabolic rate (top panel), as measured using the assay described in this patent, predicts ex vivo mammary gland lactose production (bottom panel) in response to heat stress (days 13-19 of pregnancy 35° C./50% humidity), maintenance at room temperature (RT; 22-24° C./50% humidity) with ad libitum access to feed, or maintenance at room temperature (22-24° C./50% humidity) with feed restricted to that consumed ad libitum by heat stressed animals (pair-fed; PF).

Referring to FIG. 3, mammary gland metabolic rate may be used to predict milk production. FIG. 3 shows that ex vivo mammary gland metabolic rate (top panel) predicts ex vivo mammary gland lactose production (bottom panel) in response to heat stress (days 13-19 of pregnancy 35° C./50% humidity), maintenance at room temperature (RT; 22-24° C./50% humidity) with ad libitum access to feed, or maintenance at room temperature (22-24° C./50% humidity) with feed restricted to that consumed ad libitum by heat stressed animals (pair-fed; PF).

Figure 4A:
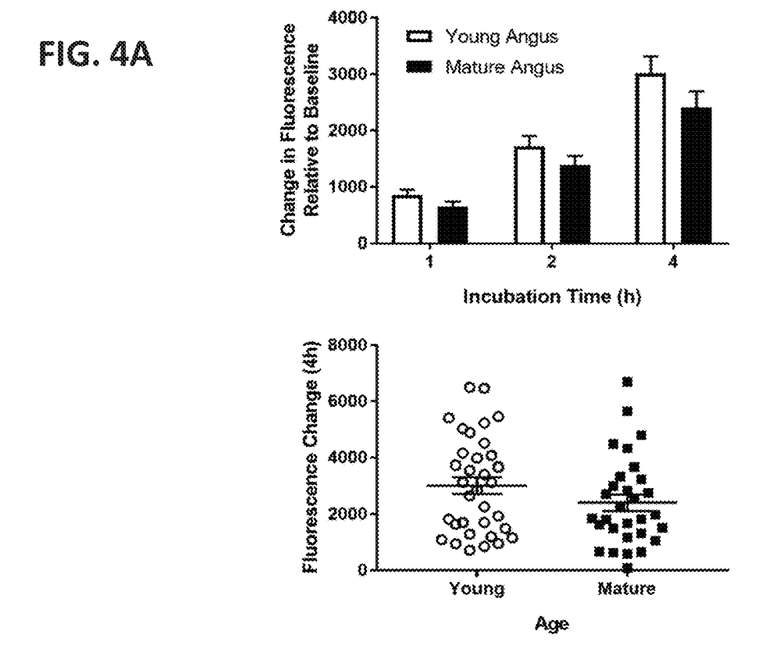
FIG. 4A shows the change in fluorescence induced by skeletal muscle biopsies (change in fluorescence relative to baseline=top panel; percent fluorescence change=bottom panel) collected from young and mature Angus cattle.
Figure 4B:
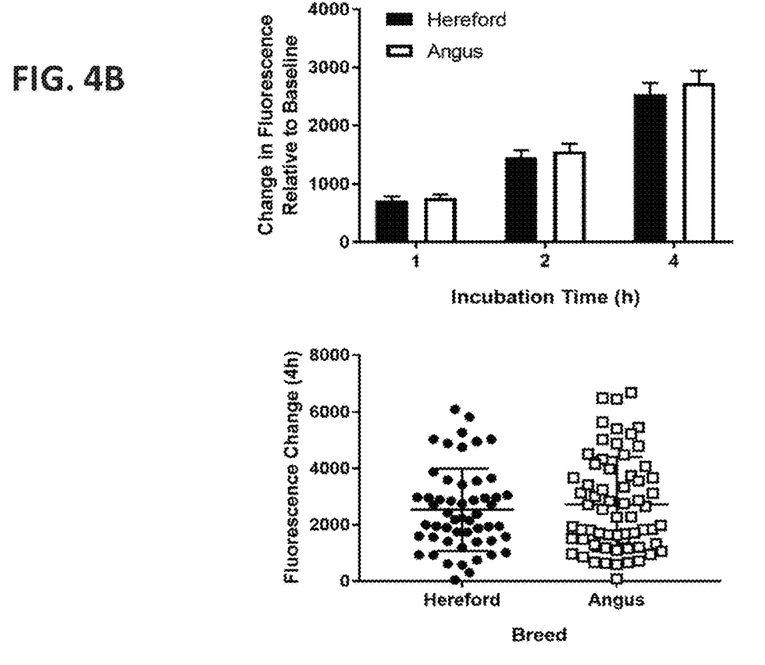
FIG. 4B shows the change in fluorescence induced by skeletal muscle biopsies (change in fluorescence relative to baseline=top panel; percent fluorescence change=bottom panel) collected from Angus and Hereford cattle. There was no breed difference in skeletal muscle metabolic rate between Hereford and Angus cattle. However, intrabreed animal-to-animal variability in skeletal muscle metabolic rate (FC/4 h) is extensive in Hereford and Angus cattle. This variability may be important for improving genetics for efficiency.

FIG. 4A and FIG. 4B show metabolic rate in young calves and fully-grown cows (Angus and Hereford). FIG. 4A shows that mature fully-grown cows have a lower metabolic rate than young growing cattle. FIG. 4B shows that there was no average difference in metabolic rate in Hereford and Angus cattle. Variability in FC/4 h is extensive in young and mature cows and in Hereford and Angus cattle. This variability is important for improving genetics for efficiency.

Thus, the effects of nutrition, nutrients, drugs, environmental stimuli, and other factors (e.g., age, etc.) on metabolic rate (e.g., tissue-specific metabolic rate) can be studied. The methods of the present invention may also be used to study the efficiency of a particular tissue important to productivity (e.g., mammary tissue important for milk production).

Obesity

The present invention also provides methods for identifying susceptibility or resistance to obesity in animals (or humans), e.g., for determining whether a subject (e.g., an animal, human, etc.) has a likelihood of developing obesity or becoming overweight, or whether the animal or human may be resistant to obesity.

As a non-limiting example, to develop a mathematical scoring function (a clinical mathematical model) to predict likelihood of developing obesity or becoming overweight), a prospective study of a cohort with known outcomes may be used develop a relationship between outcome and metabolic rate (e.g., calculate one or more candidate scoring functions, etc.). For example, a cohort of patients may be evaluated, wherein each individual provides a skeletal muscle biopsy, which is tested for metabolic rate by measuring reducing equivalent production (e.g., an amount, a change in, etc.). The resulting skeletal muscle metabolic rates may be plotted against the weight change in response to a given lifestyle intervention. Alternatively, a long-term longitudinal study could be performed to assess body weight change with time.

As a non-limiting example, outcomes may be grouped based on known standards for categorizing individuals as non-overweight, overweight, and obese. For example, in the case of humans, a body mass index (BMI) from 25.0 to 29.9 is defined as overweight, and a BMI of 30 or more is defined as obese. Thus, BMI values may be used to determine the outcomes of the individuals in the cohort.

Once a candidate scoring function is chosen, one or more cutoffs may be selected to stratify the patients into the categories described above. A non-limiting example of a mechanism for determining cutoffs of the categories may be a receiver operating characteristic (ROC) curve. ROC curves allow users to balance the sensitivity of a model (for example to prioritize capturing as many "positive" or "likely to become overweight/obese" subjects as possible) with the specificity of the model (for example minimizing false-positives for "likely to become overweight/obese candidates").

The selected scoring function (and optionally a cutoff determined by a ROC curve) provides a pre-determined threshold used for evaluating subjects being tested for susceptibility to obesity.

The present invention also features methods for selection of broodstock, e.g., selecting broodstock with high feed efficiency, selecting broodstock with high productivity, etc. The broodstock selection may feature testing a mother's or father's tissue-specific metabolic rate (e.g., skeletal muscle, etc.), which can be indicative of the feed efficiency and/or productivity of the progeny.

Effects of Drugs or Other Stimuli

The present invention also provides methods for determining an effect of genetics, environmental stimuli, a drug treatment (e.g., antibiotics), physiological treatment (e.g., exercise), a dietary supplement, a diet, or nutritional treatment on the metabolic rates (e.g., basal metabolic rate, tissue-specific metabolic rate) of animals of interest, and thus the effect on feed efficiency, productivity, etc.

For example, a group of animals (e.g., cattle) may be administered a nutritional treatment, and skeletal muscle metabolic rates may be determined to assess what effect the nutritional treatment had on the metabolic rate and potential feed efficiency, productivity, etc.

Stratifying Cattle by Skeletal Muscle NADH Reduction Rate

The present invention features high-throughput methods for assessing energy expenditure for selection to improve efficiency. For example, the methods below describe a muscle biopsy technique for stratifying cattle by skeletal muscle nicotinamide adenine dinucleotide reduction rate for assessing the metabolic rate of skeletal muscle biopsies in cattle. The technique may be applied to allow for genetic selection for growth or feed efficiency across species. The present invention is not limited to the methods, assays, and compositions described herein.

Tissue biopsy metabolic activity, assessed using the oxidation-reduction indicator Resazurin, may serve as a proxy to assess energy expenditure associated with maintenance in non-growing animals or growth rate in growing animals. These methods may evaluate the repeatability, practicality, and sensitivity of a Resazurin-based assay for ranking bovine skeletal muscle biopsies based on metabolic activity. Six yearling Holstein heifers (BW=330±11.3 kg) were fed 4 dietary treatments consisting of high or low rumen degradable starch and fiber arranged factorially in a partially replicated Latin Square design. Periods were 18 d, with 3 d diet transition, 14 d diet adaptation, and 1 d sample collection. Semitendinosus biopsies were collected into ice-cold Dulbecco's modified eagle media (DMEM) from each heifer during each period. Analysis was initiated within an hour of sample collection. To assess tissue metabolic rate, biopsies were transferred to DMEM with Resazurin and incubated at 37° C. Fluorescence of each sample was read at time 0 and at 15-minute intervals for two hours. Change in fluorescence was representative of skeletal muscle reducing equivalent production (e.g., NADH). Individual animal sample signal strength increased with increasing fluorescence time ($P<0.001$), but there was no significant interaction between time and treatment ($P>0.05$) suggesting comparison of fluorescence at a single time point would be sufficient. Change in fluorescence at 120 minutes was used for analysis of the fixed effects of fiber, starch, and animal, when accounting for a random effect of period. Samples collected when animals were on a high ruminally degradable starch diet were more metabolically active than samples collected from animals on low starch diets ($P=0.023$). Significant differences in metabolic activity among individual animals were also identified ($P=0.003$). The average relative fluorescence of each individual was paired with dry matter intake (DMI), average daily gain (ADG), and feed to gain ratio (F:G). Pearson's correlation coefficients relating the change in fluorescence to ADG and F:G were strong (ADG=0.749; F:G=−0.783) and tending toward significance (ADG $P=0.0864$; F:G $P=0.066$). The Pearson's correlation coefficient for the relationship between DMI and change in fluorescence was much weaker (0.153) and was non-significant ($P=0.773$). Thus, this method can rank individual animals based on metabolic activity and detect differences in metabolic activity associated with dietary changes.

Treatment Diets and Adaptation Period

Six ruminally cannulated yearling Holstein heifers (BW=330±11.3 kg) were randomly assigned to 4 dietary treatments in a partially replicated Latin Square design. For each period, two treatments were duplicated and the other two treatments were not. Periods were 18 d in length. The first 3 d were used to adapt animals between rations, animals consumed the treatment ration for 14 d, and samples were collected on the final day. Diets were factorially designed with corn silage as a base (29.4-35.6, % DM), and used combinations of ground barley (high rumen degradable starch (HS) 14.1-14.8, % DM; low rumen degradable starch (LS) 0.310-0.670, % DM) or corn (HS 0.00-0.380, % DM; LS 10.5-12.3, % DM) and pelleted beet pulp (high rumen degradable fiber (HF) 3.55-6.05, % DM; low rumen degradable fiber (LF) 30.2-32.9, % DM) or timothy hay (HF 19.9-25.0, % DM; LF 0.020-1.43, % DM) to generate rations with high and low ruminal degradable starch and fiber. As described in Table 1 below, diets also contained soybean meal (HS-HF 9.3, % DM; HS-LF 17.1, % DM; LS-HF 9.95, % DM; LS-LF 15.3, % DM), blood meal (HS-HF 3.78, % DM; HS-LF 0.00, % DM; LS-HF 4.37, % DM; LS-LF 0.040, % DM), and corn gluten feed (HS-HF 3.26, % DM; HS-LF 0.00, % DM; LS-HF 1.65, % DM; LS-LF 7.22, % DM) to make them isonitrogenous. These treatment combinations resulted in divergent energy supply to the animals, and the calculated metabolic energy (ME) for each ration is included in Table 1.

TABLE 1

Ingredients and nutrient composition for each treatment diet expressed on a dry matter basis.

|  | HS-LF[1] | HS-HF[2] | LS-LF[3] | LS-HF[4] |
|---|---|---|---|---|
| Ingredients, % DM |  |  |  |  |
| Timothy Hay | 0.020 | 19.9 | 1.43 | 25.0 |
| Beet Pulp | 30.2 | 6.05 | 32.9 | 3.55 |
| Ground Corn | 0.000 | 0.380 | 12.3 | 10.5 |
| Ground Barley | 14.8 | 14.1 | 0.310 | 0.670 |
| Corn Silage | 35.6 | 34.4 | 29.4 | 35.2 |
| Corn Gluten Feed | 0.000 | 3.26 | 7.22 | 1.65 |
| Soybean Meal | 17.1 | 9.3 | 15.3 | 9.95 |
| Blood Meal | 0.000 | 3.78 | 0.040 | 4.37 |
| Vitamin E Premix |  |  |  |  |
| Vitamin A-D3 Premix |  |  |  |  |
| Nutrient, % DM |  |  |  |  |
| DM | 73.4 | 64.8 | 74.7 | 63.9 |
| OM |  |  |  |  |
| NDF | 35.0 | 35.0 | 35.0 | 35.0 |
| ADF |  |  |  |  |
| Starch | 20.0 | 20.0 | 20.0 | 20.0 |
| CP | 16.0 | 15.9 | 16.0 | 15.9 |
| Estimated ME, Mcal/kg | 2.74 | 2.63 | 2.75 | 2.62 |

[1]HS-LF = high rumen degradable starch, low fiber treatment
[2]HS-HF = high rumen degradable starch, high fiber treatment
[3]LS-LF = low rumen degradable starch; low fiber treatment
[4]LS-HF = low rumen degradable starch; high fiber treatment Sample Preparation and Collection A 10 cm wide area 5 cm to 35 cm ventral to the point of the ischium was shaved and scrubbed three times with betadine and isopropanol. 10 ml of lidocaine was administered subcutaneously in 5 to 6 locations radially arrayed 2 cm externally to the biopsy site. The target biopsy site was 20 cm ventral to the point of the ischium. Muscle tissue samples were collected by making a 1 cm incision through the skin with a #20 scalpel blade, inserting a 20 gauge biopsy needle (Bard® Mission® Disposable Core Biopsy Instrument) to a 4 cm depth, and depressing the needle collection sheath to obtain a sample. Three biopsies, with the aim of obtaining approximately 30 mg of sample, were collected per animal per period to evaluate how variation in sample collection (sample mass, collection site within the muscle, and other unknown factors) influenced consistency of the results. Samples were not weighed after collection because an analytical balance was not available at the farm. The incision site was sealed using monofilament #2 suture wire, cleaned with isopropanol, and sprayed with adhesive bandage. The right semitendinosus was sampled in periods 1 and 3 and the left semitendinosus was sampled in periods 2 and 4.

Immediately following collection, the structurally intact core samples were placed in individual wells of a 96 well plate filled with a pre-test solution. The pre-test solution and contained 30 ml DMEM (Fisher Science 21-041-025), 7.5 mg Fungizone (Fisher Science 15-290-026), 0.12 mg Chloramphenicol (Fisher Science BP904-100), and 0.03 mg Ampicillin (Fisher Science AAJ6097714). After all samples were collected, they were transferred from the pre-test solution into individual wells of a 96 well plate filled with resazurin test assay solution. The test solution was identical to the pre-test solution with 1.6% AlamarBlue® (resazurin-based reagent, Thermo Scientific Y00-100) added. Solutions were mixed immediately prior to biopsy collection, filtered using a sterile 0.22 µM filter, and warmed to 37° C. before use.

Sample Analysis

Directly after sample collection, the live muscle tissue samples were transported to the lab in the pre-test solution, transferred to the test solution, and analyzed. Analysis was initiated within one hour of tissue collection to ensure tissue viability. When samples were transferred to the test solution, the test solution plate was incubated in the plate reader (Spectramax M5; Molecular Devices, LLC, San Jose, Calif.) at 37° C. Fluorescence was read at time 0 and every 15 minutes for 2 hours using excitation and emission wavelengths of 530 and 590 nm, respectively. Soft Max Pro 6.1 (Molecular Devices, LLC, San Jose, Calif.) was used to quantify resulting emissions, and relative fluorescence (standardized to time 0) was calculated at each time point for each sample.

Consistency of Samples within Animal-Periods

Triplicate samples were collected within an animal-period to evaluate the consistency of animal rankings obtained from like samples. The within-animal-period CV for relative fluorescence was approximately 20%, suggesting a need to standardize samples by protein or DNA content or by mass. Despite the degree of variation among samples collected from the same animal consuming the same diet, a Wilcoxon rank sum test did not find significant differences in the rankings of animals when different individual samples were used (P>0.05) suggesting this variation did not impede opportunities to rank animals by skeletal muscle metabolic activity.

Statistical Analysis

Mean relative fluorescence was calculated for each animal-period at each time point. Statistical analysis of the mean fluorescence data was conducted in R version 3.1.0. (R Core Team, 2014). Analysis was structured into 2 questions: 1) does the incubation time change the perceived influence of a treatment on relative NAD$^+$ reduction rate; and 2) are differences between animals and treatments discernable after 2 h. To address the first question, a linear mixed effect model was used to test how time, fiber and starch digestibility, animal, and period influenced standardized fluorescence readings. Fiber, starch and time were fixed effects, and the 2- and 3-way interactions among these fixed effects were also evaluated. Period and animal were treated as random effects. A significant time by starch or fiber interaction would suggest that treatment differences were not consistent across a sampling period and some ideal fluorescence reading time would need to be determined to make reliable inferences from the data. To address the second question, data from the last time point (2 h) was analyzed using a linear mixed effect model with fixed effects of fiber, starch, and animal and a random effect of period. Significant starch, fiber or animal effects would suggest that the assay (using only a 2 h fluorescence time) was sensitive enough to rank samples based on animal-level factors (genetic potential or diet).

Time

Figure 5:
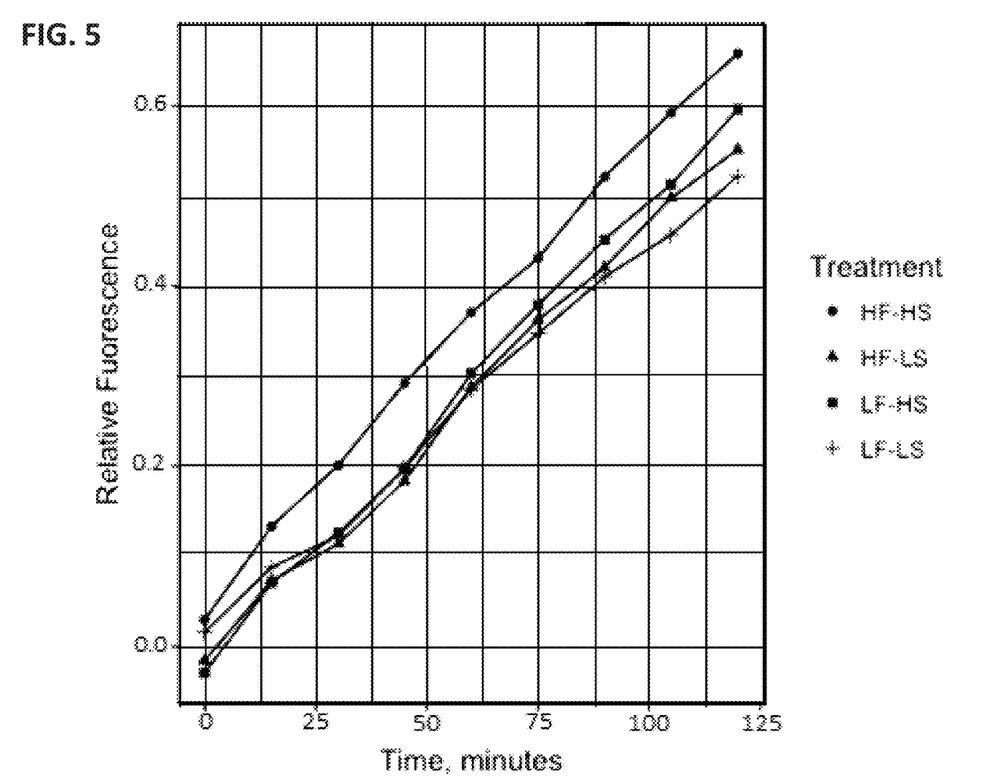
FIG. 5 shows the skeletal muscle biopsies induce a relative change in fluorescence, equivalent to cumulative energy expenditure over time, that increases throughout a 2-h incubation period and differs based on the diet fed to steers high fiber-high starch (HF-HS), high fiber-low starch (HF-LS), low fiber-high starch (LF-HS), and low fiber-low starch (LF-LS) diets. This establishes that this test can be applied to understand the effect of diet on tissue specific metabolic rate within cattle.

Because the plate can be read at multiple time points, the effect of time on within-sample fluorescence tested (see FIG. 5). The reduction reaction that causes Resazurin to fluoresce is irreversible, and as a result the signal accumulates with time allowing small short-term differences to amass as time of incubation is extended. The total signal increased linearly with time (P<0.0001), which suggests that the tissue biopsies continued to metabolize at a constant rate throughout the incubation period. Time did not differentially affect fluorescence based on starch (P=0.5106) or fiber (P=0.8072) in the diet, supporting the conclusion that the rankings of samples were similar if evaluated at any time point within the 2 hours.

Diet

Skeletal muscle biopsies taken when heifers were on a high ruminally degradable starch diet had a higher relative fluorescence than biopsies taken when heifers were fed a diet low in ruminally degradable starch (P=0.023). The link between starch source and skeletal muscle metabolic activity could be caused by a change in energy availability. However, calculated ME in the diets changed more with rumen degradable fiber than with rumen degradable starch, making this explanation unlikely. Alternatively, the increase in tissue metabolic activity with increased ruminally degradable starch may be related to a different absorbed volatile fatty acid profile. Different VFA are used for energy with different efficiencies in the post-absorptive system. Approximate VFA contribution to muscle is dependent upon individual VFA metabolism. Less than 30% of acetate, 40-55% of propionate, and minimal butyrate is available to the periphery. Glucose contribution to skeletal muscle in ruminants is due to gluconeogenesis. Hepatic uptake of propionate, valerate, and isobutyrate allows for increased gluconeogenic substrate. If the different starch sources contributed to different profiles of absorbed VFA, it is possible that the absorbed VFA profiles contributed to the effect of ruminally degradable starch on skeletal muscle metabolic activity. Independent of the mechanism driving this dietary effect, the results suggest the assay can be applied to understand the metabolic effects of ration changes.

Animal

Figure 6:
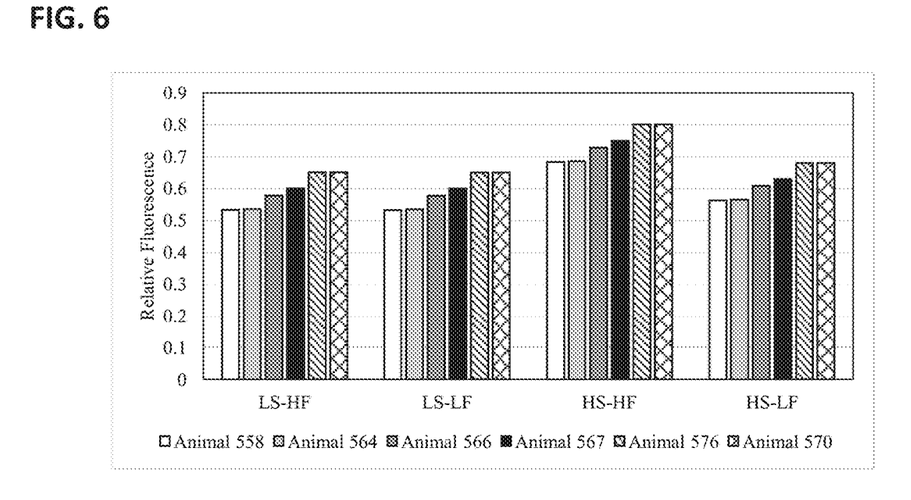
FIG. 6 establishes that the relative rank of animals based on skeletal muscle metabolic rate was maintained across dietary treatments. Treatments included either a high (HS) or low (LS) rumen degradable starch source and either a high (HF) or low (LF) rumen degradable fiber source. Animal numbers are arbitrary and reflect the animal identifier assigned by the farm. These identifiers are included in the legend to show consistence of animal rankings across diets. This figure establishes that rankings of similarly treated animals based on skeletal muscle metabolic rate can effectively be maintained independent of diet.

Comparisons among animals show that skeletal muscle metabolic activity varied between individuals (P=0.003). The effect of diet was consistent amongst animals, and animals ranked similarly across diets (see FIG. 6). This consistency suggests that inherent differences in skeletal muscle metabolic activity may be distinguishable across conditions, making it a possible way to inexpensively and durably screen animals for energy expenditure associated with growth or in non-growing animals, maintenance.

Figure 7:
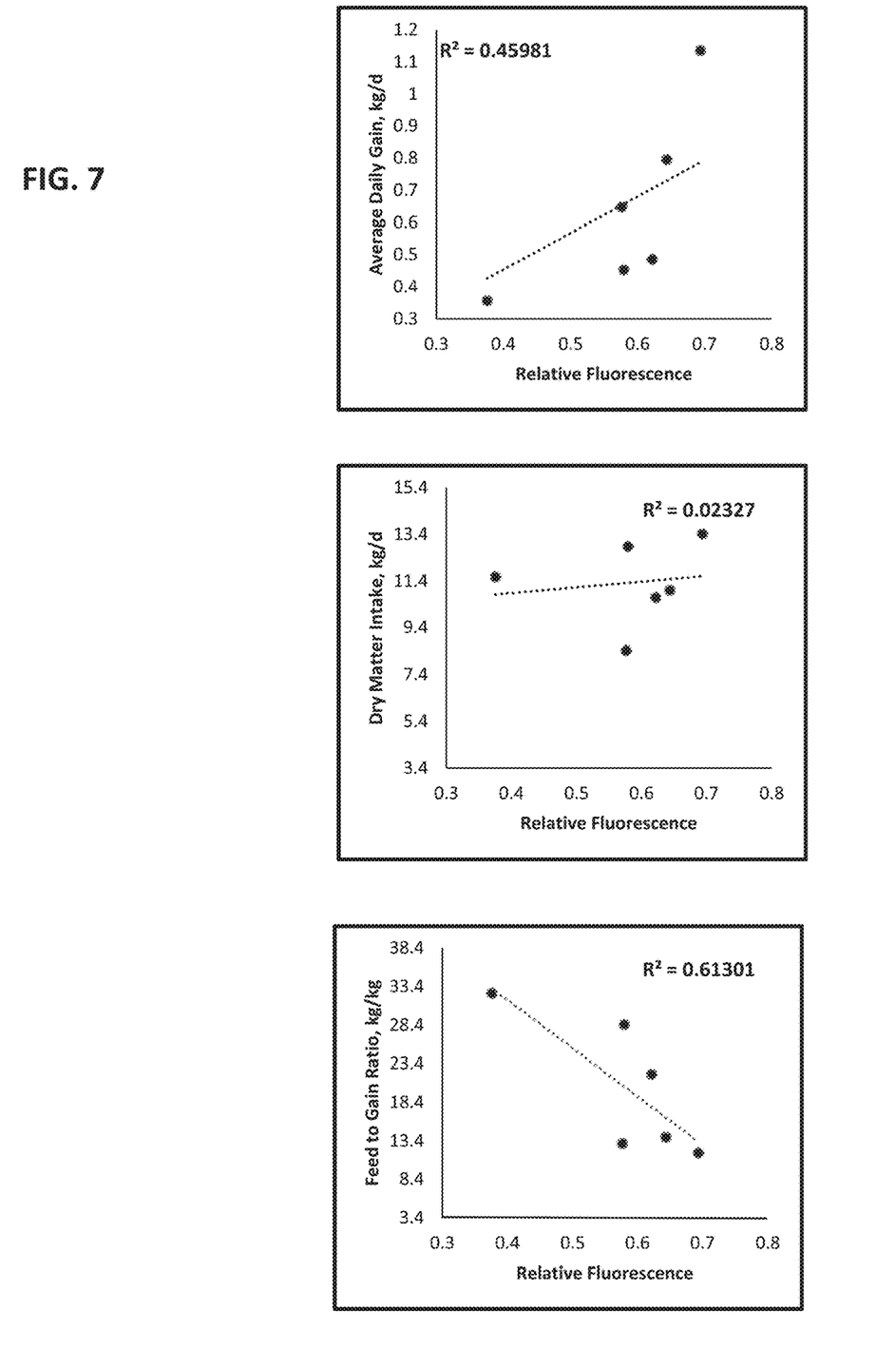
FIG. 7 shows the skeletal muscle metabolic rate of growing steers (as indicated on the X-axis, relative fluorescent change) is directly related to average daily gain (ADG) (top panel), does not relate to mean dry matter intake (DMI) (middle panel), and is inversely related to feed to gain ratio (F:G) (bottom panel). (Each dot represents an individual animal.) The dotted line shows a best-fit linear regression of the performance variable on relative fluorescence. The $R^2$ values presented reflect the coefficient of determination for each regression. This data establishes that skeletal muscle reducing equivalent (NADH, $FADH_2$, etc.), used as a proxy for tissue metabolic rate, can be used to predict growth and feed efficiency in a growing animal.

The metabolic activity of a ruminant is a function of body mass and metabolic flux during an inactive, thermoneutral environment. These differences in metabolic flux contribute to variability in feed efficiency. The individual metabolic flux can be influenced by genetic potential, activity and behavior, environment, and heifer rearing practices. Referring to FIG. 7, the average skeletal muscle metabolic activity (expressed as relative fluorescence) of each individual was paired with dry matter intake (DMI), average daily gain (ADG), and calculated feed to grain ratio (F:G). Pearson's correlation coefficients relating the change in fluorescence to ADG and F:G were strong (ADG=0.749; F:G=-0.783) and tending toward significance (ADG P=0.0864; F:G P=0.066). The Pearson's correlation coefficient for the relationship between DMI and change in fluorescence was much weaker (0.153) and was non-significant (P=0.773).

Skeletal muscle biopsy metabolic activity was indicative of energy expenditure for growth and maintenance in these young, rapidly growing heifers. The positive correlation with growth and feed to gain ratio in these studies suggests that the measure of metabolic activity was more heavily influenced by energy expenditure for growth than energy expenditure for maintenance. Samples taken from mature animals may more effectively address the genetic potential for feed efficiency. Given the fact that the assay was sufficiently sensitive to detect between-animal differences, it can be a useful screening tool to allow for genetic selection based on feed efficiency in mature cattle at maintenance.

Example 1

The following example describes a method of identifying an animal with high feed efficiency. The present invention is not limited to the methods and compositions described herein.

A rancher owns a population of cattle and is interested in choosing the animals with the highest feed efficiency for breeding purposes. For each adult animal, she obtains a skeletal muscle tissue sample and measures the metabolic rate by measuring reducing equivalents.

The metabolic rate of the skeletal muscle tissue is inversely related to the feed efficiency, so the farmer chooses to breed the animals with the metabolic rates that are in the lowest 25%, which would have the highest feed efficiency. For example, for a group of 100 animals, the rancher chooses the 25 animals with the lowest skeletal muscle metabolic rate. Those animals in the $25^{th}$ percentile are selected for breeding purposes. The remaining 75% of the animals are not used for breeding.

Example 2

The following example describes a method of identifying an animal with high milk production. The present invention is not limited to the methods and compositions described herein.

A farmer owns a population of cattle and is interested in choosing the animals with the highest milk production for breeding purposes. For each animal, he obtains a mammary tissue sample and measures the metabolic rate by measuring reducing equivalents.

The metabolic rate of the mammary tissue is directly related to the potential milk production. The farmer has previously done studies to determine the amount of milk produced per day (gallons per day) based on a particular metabolic rate of mammary tissue. For example, a metabolic rate of 1000 (fluorescence change per mg tissue) or more predicts the animal will produce at least 6 gallons of milk per day. A metabolic rate of 2000 (fluorescence change per mg tissue) or more predicts the animal will produce at least 9 gallons of milk per day. A metabolic rate of 3000 (fluorescence change per mg tissue) predicts the animal will produce at least 12 gallons per day.

Half of the cows have a metabolic rate of 1000 (fluorescence change per mg tissue) or less. Only 10% of the cows have a metabolic rate of 2000 (fluorescence change per mg tissue) or more, and the farmer chooses only those animals, which are expected to produce at least 9 gallons of milk per day.

Example 3

The following example describes a method for detecting an effect of a drug on feed efficiency of an animal. The present invention is not limited to the methods and compositions described herein.

A rancher owns 40 cattle and is interested in determining how Drug A will affect the feed efficiency of the cattle. For each animal, she obtains a skeletal muscle tissue sample and measures the metabolic rate by measuring reducing equivalents. She calculates the average metabolic rate for the group of animals.

She subsequently administers Drug A to 20 animals once a day for two weeks and a placebo to the remaining 20 animals. At the end of the two weeks, she obtains skeletal muscle tissue samples from each animal and measures the metabolic rate by measuring reducing equivalents. She calculates the average metabolic rate for the group of animals treated with Drug A and the average metabolic rate for the group of animals given the placebo.

The rancher calculates that treatment with Drug A lowered the average metabolic rate of the animals by 20%. This correlates with a 20% change in average feed efficiency of the animals as well.

Example 4

The following example describes a method for detecting an effect of a drug on milk production of an animal. The present invention is not limited to the methods and compositions described herein.

A farmer owns 100 cows and is interested in determining how Drug B will affect milk production of the animals. For each animal, he obtains a mammary tissue sample and measures the metabolic rate by measuring reducing equivalents. He calculates the average metabolic rate for the group of animals.

He subsequently administers Drug B to 50 animals twice a day for four weeks and a placebo to the remaining 50 animals. At the end of the four weeks, he obtains mammary tissue samples from each animal and measures the metabolic rate by measuring reducing equivalents. She calculates the average metabolic rate for the group of animals treated with Drug B and the average metabolic rate for the group of animals given the placebo.

The farmer calculates that treatment with Drug B increased the average metabolic rate of the animals by 10%. This correlates with a 10% increase in milk production.

The disclosures of the following U.S. patents are incorporated in their entirety by reference herein: PCT/US16/48006.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method of identifying and using an animal with high feed efficiency, said method comprises
   determining reducing equivalent production in a skeletal muscle tissue sample from the animal, wherein the reducing equivalent production in the skeletal muscle tissue sample is inversely related to feed efficiency, wherein if the reducing equivalent production in the skeletal muscle tissue sample is below a predetermined threshold, then the animal from which the skeletal muscle tissue sample was obtained has a high feed efficiency compared to animals having reducing equivalent production above the predetermined threshold, wherein the reducing equivalent production is NADH; and
   breeding the animal identified as having high feed efficiency or using the animal identified as having high feed efficiency for production of an animal product.

2. The method of claim 1, wherein the predetermined threshold is an average of reducing equivalent production for a breed, herd, or species of the animal.

3. The method of claim 1, wherein the predetermined threshold stratifies animals by feed efficiency.

4. The method of claim 1, wherein determining reducing equivalent production in the skeletal muscle tissue sample comprises introducing a reducing equivalent indicator to the tissue sample or media in which the tissue sample is incubating and measuring an amount of or a change in reducing equivalent indicator, which is indicative of metabolic activity.

5. The method of claim 1, wherein the animal product is eggs, milk or meat.

* * * * *